(12) United States Patent
Alcalde-Pais et al.

(10) Patent No.: US 8,138,210 B2
(45) Date of Patent: Mar. 20, 2012

(54) SUBSTITUTED INDANYL SULFONAMIDE COMPOUNDS, THEIR PREPARATION AND USE AS MEDICAMENTS

(75) Inventors: Maria De Las Ermitas Alcalde-Pais, Barcelona (ES); Maria De Les Neus Mesquida-Estevez, Barcelona (ES); Sara Lopez-Perez, Barcelona (ES); Jordi Frigola-Constansa, Barcelona (ES); Joerg Holenz, Barcelona (ES); Ramon Merce-Vidal, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 1611 days.

(21) Appl. No.: 11/506,352

(22) Filed: Aug. 18, 2006

(65) Prior Publication Data

US 2008/0027073 A1  Jan. 31, 2008

(30) Foreign Application Priority Data

Jul. 31, 2006 (EP) .................................. 06380220

(51) Int. Cl.
C07D 277/82 (2006.01)
C07C 281/06 (2006.01)
A61K 31/425 (2006.01)
A61K 31/16 (2006.01)

(52) U.S. Cl. ........ 514/368; 514/590; 548/161; 548/167; 564/36

(58) Field of Classification Search .................. 548/161, 548/167; 514/368, 590; 564/36
See application file for complete search history.

(56) References Cited

U.S. PATENT DOCUMENTS 7,893,069 B2 * 2/2011 Kuehnert et al. ............. 514/256

FOREIGN PATENT DOCUMENTS

| EP | 0456 133 A1 | 5/1991 |
| EP | 0538 193 A2 | 10/1992 |
| EP | 0747 374 A1 | 6/1996 |
| WO | 9602537 A1 | 2/1996 |
| WO | 9611929 | 4/1996 |
| WO | 9623783 | 8/1996 |
| WO | 9708167 | 3/1997 |

OTHER PUBLICATIONS

D. Hoyer et al., "5-HT Receptor Classification and Nomenclature: Towards a Harmonization with the Human Genome," Neuropharmacology; (1997) vol. 36, No. 4/5, pp. 419-427.
F. Monsma, Jr. et al., "Cloning and Expression of a Novel Serotonin Receptor with High Affinity for Tricyclic Psychotropic Drugs," Molecular Pharmacology; (1993) 43:320-327.
M. Ruat et al., "A Novel Rat Serotonin (5-HT6) Receptor: Molecular Cloning, Localization and Stimulation of Camp Accumulation," Biochem. Biophys. Res. Commun.; (1993) vol. 193, No. 1, pp. 168-276.
R. Kohen et al., "Cloning, Characterization, and Chromosomal Localization of a Human 5-HT6 Serotonin Receptor," J. Neurochemistry, (1996) vol. 66, No. 1, pp. 47-56.
M. Yoshioka et al., "Central Distribution and Function of 5-ht6 Receptor Subtype in the Rat Brain," Ann, NY Acad. Sci.; (1998) 861, pp. 244-.
A. Bourson et al., "Involvement of 5-HT6 receptors in nigro-striatal function in rodents," Br. J. Pharmacology (1998) 125, pp. 1562-1566.
A. Bourson et al., "Determination of the Role of the 5-ht6 Receptor in the Rat Brain: A Study using Antisense Oligonucleotides," J. Pharmacol. Exp. Ther., (1995) pp. 173-180.
A.J. Sleight et al., "Effects of altered 5-ht6 expression in the rat: functional studies using antisense oligonucleotides," Behavioural Bran Research, 73 (1996) pp. 245-248.
T. A. Branchek et al., "5-HT6 Receptors as Emerging Targets for Drug Discovery," Annu. Rev. Pharmacol. Toxicol, (2000) 40:319-34.
C. Routledge et al., "Characterization of SB-271045: A potent, selective and orally active 5-HT6 receptor antagonist," Br. J. Pharmacol., (2000) 130, pp. 1606-1611.
B. L. Roth et al., "Binding of Typical and Atypical Antipsychotic Agents to 5-Hydroxytryptamine-6 and 5-Hydroxytryptamine-7 Receptors," J. Pharmacol. Exp. Ther., (1994) vol. 268, pp. 1403-1410.
C. E. Glatt et al., "Clozapine: Selective Labelling of Sites Resembling 5HT6 Serotonin Receptors May Reflect Psychoactive Profile," Molecular Medicine, vol. 1, No. 4, May 1995, pp. 398-406.
F. J. Monsma, Jr. et al., "Cloning and Expression of a Novel Serotonin Receptor with High Affinity for Tricyclic Psychotropic Drugs," Molecular Pharmacology, (1993) 43:320-327.
T. Shinkai et al., "Associate Study of teh 5-HT6 Receptor Gene in Schizophrenia," Am. J. Med. Gen., (1999) 88:120-122.
C. Gerard et al., "Immuno-localization of serotonin 5-HT6 receptor-like material in the rat central nervous system," Brain Res., 746 (1997) pp. 207-219.
M.R. Pranzatelli, M.D., "Serotonergic Drugs and Movement Disorders in Humans," Drugs of Today, 33(6), 1997 pp. 379-392.

(Continued)

*Primary Examiner* — Peter O Sullivan
(74) *Attorney, Agent, or Firm* — Fulwider Patton LLP

(57) ABSTRACT

The present invention refers to new indanyl sulphonamide compounds with general formula (I), as well as to their preparation procedure, their application as medicine and the pharmaceuticals composition which they are made up of.

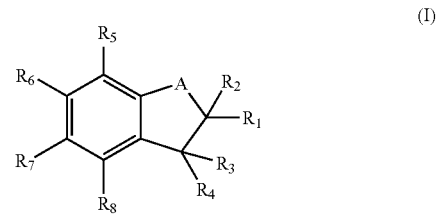

(I)

The new compounds of formula I show affinity for 5-HT$_6$ receptors and are, therefore, effective for treating diseases mediated by these receptors.

13 Claims, No Drawings

OTHER PUBLICATIONS

M.L. Woolley et al., "A role for 5-ht6 receptors in retention of spatial learning in the Morris water maze," Neuropharmacology, (2001) 41:210-219.

P.J. Munson et al., "LIGAND: A Versatile Computerized Approach for Characterization of Ligand-Ginding Systems," Anal. Biochem, 107 (1980) pp. 220-239.

D.C. Rogers et al., "Cognitive Enhancement Effects of the Selective 5-HT6 Antagonist SB-271046," Br. J. Pharmacol. Suppl. 1999, 127, 22P.

W.D. Hirst et al., "Characterization of [125I]-SB-258585 binding to human recombinant and native 5-HT6 receptors in rat, pig and human brain tissue," Br. J. PharmacoL, 2000, 130, pp. 1597-1605.

* cited by examiner

SUBSTITUTED INDANYL SULFONAMIDE COMPOUNDS, THEIR PREPARATION AND USE AS MEDICAMENTS

FIELD OF THE INVENTION

The present invention relates to new indanyl sulfonamide compounds with a general formula (I), as well as to their process of preparation, their application as medicaments and to pharmaceutical compositions comprising them.

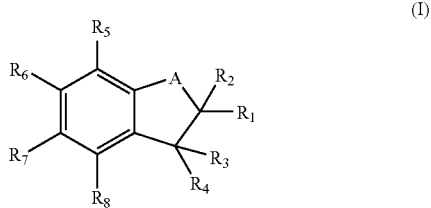
(I)

The new compounds of formula I show affinity for $5\text{-}HT_6$ receptors and are, therefore, effective for treating diseases mediated by these receptors.

BACKGROUND OF THE INVENTION

The superfamily of 5-HT serotonin receptors includes 7 classes ($5\text{-}HT_1\text{-}5\text{-}HT_7$) which encompass 14 subclasses [D. Hoyer, et al., *Neuropharmacology*, 1997, 36, 419]. The $5\text{-}HT_6$ receptor is the latest serotonin receptor identified by molecular cloning both in rats [F. J. Monsma, et al., *Mol. Pharmacol.*, 1993, 43, 320; M. Ruat, et al., *Biochem. Biophys. Res. Commun.*, 1993, 193, 268] and humans [R. Kohen, et al., *J. Neurochem.*, 1996, 66, 47]. Compounds that show affinity for $5\text{-}HT_6$ receptors are suitable for the treatment of several disorders of the central nervous system and the gastrointestinal tract, such as irritable bowel syndrome. Compounds with affinity for $5\text{-}HT_6$ receptors are also suitable for treating anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that typical and atypical antipsychotic drugs used to treat schizophrenia have a high affinity for $5\text{-}HT_6$ receptors [B. L. Roth, et al., *J. Pharmacol. Exp. Ther.*, 1994, 268, 1403; C. E. Glatt, et al., *Mol. Med.*, 1995, 1, 398; F. J. Mosma, et al., *Mol. Pharmacol.*, 1993, 43, 320; T. Shinkai, et al., *Am. J. Med. Genet.*, 1999, 88, 120]. Compounds with affinity for $5\text{-}HT_6$ receptors are also suitable for treating infantile hyperkinesia (ADHD; Attention Deficit/Hyperactivity Disorder) [W. D. Hirst, et al., *Br. J. Pharmacol.*, 2000, 130, 1597; C. Gérard, et al., *Brain Research*, 1997, 746, 207; M. R. Pranzatelli, *Drugs of Today*, 1997, 33, 379]. It has also been shown that $5\text{-}HT_6$ receptors also play a role in the intake of nutrients [*Neuropharmacology*, 2001, 41, 210-219]. Eating disorders, particularly obesity, are a serious and growing threat to public health in all age groups, as they increase the risk of developing other more serious diseases that endanger the life of patients, such as diabetes or coronary diseases.

Several patent documents refer to compounds with affinity for receptors of the 5-HT superfamily. Documents WO 96/23783, WO 96/02537, WO 96/11929 and WO 97/08167 describe heterocyclic compounds antagonists of 5-HT2b/2c receptors.

On another hand, there are other patent documents that have described indanyl sulphonamide compounds and other indanyl derivatives with therapeutic activity. Patent EP 0747374 describes among others indanyl sulphonamide compounds with potassium channel activating activity that makes them useful as cardiovascular agents. In EP 538193 and EP 456133 some indanyl derivatives with S-adenosil-methyonine-descarboxilase inhibitory activity are also described.

Surprisingly, the authors of the present invention have observed that indanyl sulphonamide compounds with general formula (I) show an affinity for $5\text{-}HT_6$ receptors ranging from good to excellent. These compounds are therefore particularly suitable as pharmacologically active agents in medicaments for the prophylaxis and/or treatment of disorders or diseases related to $5\text{-}HT_6$ receptors.

OBJECT OF THE INVENTION

First of all, an object of the present invention is an indane derivative of general formula (I):

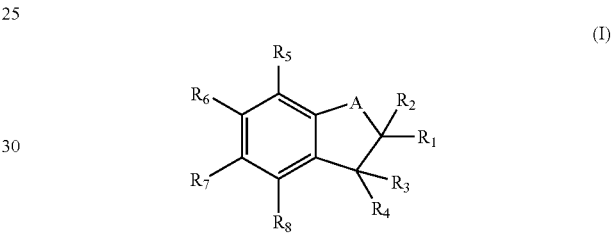
(I)

Compounds with general formula (I) have shown a high affinity for $5HT_6$ receptors and thus provide a good therapeutic alternative for treating disorders mediated by said receptors.

Another object of the present invention is the processes for preparing the indanyl sulfonamide compounds of general formula (I). As will be seen further below, the present application describes the processes for obtaining the compounds (Ia) and (Ib) specific embodiments of the compounds of general formula I.

An additional object of the present invention is the intermediates of general formula (II):

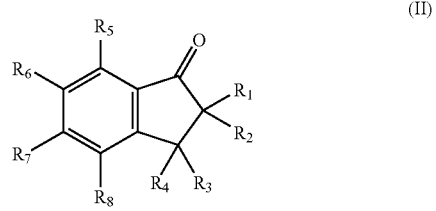
(II)

for obtaining the compounds of formula (I)

Likewise, the use of indanyl sulfonamide compounds of general formula (I) in the manufacture of a medicament for treating disorders or diseases mediated by $5HT_6$ receptors is an object of the present invention. Among the diseases or disorders mediated by $5HT_6$ receptors for which indanyl sulphonamide compounds of general formula I are useful are disorders or diseases related to food intake, preferably those related to appetite regulation, maintaining, increasing or reducing body weight, obesity, bulimia, anorexia, cachexia or diabetes type II, or irritable bowel syndrome; disorders of the central nervous system; anxiety; panic attacks; depression; bipolar disorders; cognitive disorders; memory disorders; senile dementia; psychosis; schizophrenia; neurodegenerative disorders, preferably selected among Alzheimer's disease, Parkinson's disease, Huntington's disease and multiple sclerosis; or hyperactivity disorders, preferably attention deficit/hyperactivity disorder or for improving cognitive capacity.

A final object of the present invention is a pharmaceutical composition comprising indanyl sulphonamide compounds of general formula I and at least one pharmaceutically acceptable additive. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, oral, sublingual, nasal, percutaneous, vaginal, oral or parenteral application.

DETAILED DESCRIPTION OF THE INVENTION

A first aspect of the invention refers to indanyl sulfonamide compounds of general formula I:

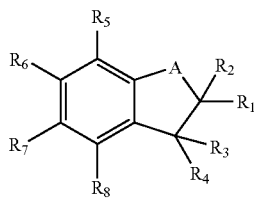

(I)

wherein
$R^1$, $R^2$, $R^3$, $R^4$, independent from one another, each represent an hydrogen atom; or a linear or branched, saturated or unsaturated $C_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$;
$R^5$, $R^6$, $R^7$ and $R^8$, independent from one another, each represent a hydrogen atom; —NO$_2$; —NH$_2$; —SH; —OH; —CN; —C(=O)—H; —C(=O)—R$^{10}$; —OR$^{11}$; —SR$^{12}$; —S(=O)$_2$—N(R$^{14}$)R$^{15}$; —N(R$^{16}$)—S(=O)$_2$—R$^{17}$; —NH—R$^{18}$; —NR$^{19}$R$^{20}$; F; Cl; Br; I; a linear or branched, saturated or unsaturated $C_{1-6}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$; or a 5- to 14-membered aryl or heteroaryl radical, which may be substituted with 1, 2 or 3 substituent(s) independently selected from the group consisting of —CF$_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —OCF$_3$, —SCF$_3$, —OH, —SH, —NH$_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —NO$_2$, —CHO, —CF$_2$H, —CFH$_2$, —C(=O)—NH$_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched $C_{1-6}$ alkylene group and wherein the heteroaryl radical contains 1, 2 or 3 heteroatom(s) independently selected from the group consisting of nitrogen, oxygen and sulfur as ring member(s);
with the condition that at least one of the substituents $R^5$, $R^6$, $R^7$ and $R^8$ represents a —S(=O)$_2$—N(R$^{14}$)R$^{15}$ or a —N(R$^{16}$)—S(=O)$_2$—R$^{17}$ radical;

A represents $$C=N-N(H)-R_{23} \quad \text{or} \quad C(R_{24})-N(R_9)-[N]_n-N(R_{9a})(R_{9b})$$
$$\hspace{2.2cm} X \hspace{4.5cm}$$

which respectively means (Ia) and (Ib) type compounds:

(Ib)

(Ia)

wherein
n is 1, 2, 3 or 4
X represents NH, O or S
$R^{23}$ represents NH$_2$ or NH—NH$_2$
$R^{24}$ represents a hydrogen atom; or a linear or branched, saturated or unsaturated $C_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$
$R^9$ and $R^{9a}$, independent from one another, each represent a hydrogen atom; or a linear or branched, saturated or unsaturated $C_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$;
or
$R^9$ and $R^{9a}$ together with the bridging nitrogen atoms form a saturated, unsaturated or aromatic 3- to 9-membered heterocyclic ring which may be substituted with 1, 2 or 3 substituent(s) independently selected from the group consisting of $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —CF$_3$, —OCF$_3$, —SCF$_3$, —OH, —SH, —NH$_2$, —NH(C$_{1-5}$-alkyl), —N(C$_{1-5}$-alkyl)$_2$, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl and which may contain 1, 2 or 3 additional heteroatom(s) independently selected from the group consisting of nitrogen, oxygen and sulfur as a ring member(s)

R$^{9b}$ represent a hydrogen atom; or a linear or branched, saturated or unsaturated C$_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$ R$^{10}$ to R$^{22}$, independent from one another, each represent a hydrogen atom; a linear or branched, saturated or unsaturated C$_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$; a saturated or unsaturated 3 to 8-membered cycloaliphatic radical, which may be substituted with 1, 2 or 3 substituent(s) independently selected from the group consisting of C$_{1-5}$-alkyl, —O—C$_{1-5}$-alkyl, —S—C$_{1-5}$-alkyl, oxo (=O), thioxo (=S), —C(=O)—OH, —C(=O)—O—C$_{1-5}$-alkyl, —O—C(=O)—C$_{1-5}$-alkyl, F, Cl, Br, I, —CN, —CF$_3$, —OCF$_3$, —SCF$_3$, —OH, —SH, —NH$_2$, —NH(C$_{1-5}$-alkyl), —N(C$_{1-5}$-alkyl)$_2$, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl, cyclopropyl, cyclobutyl, cyclopentyl, cyclohexyl, phenyl, phenoxy and benzyl and which may optionally contain 1, 2 or 3 heteroatom(s) independently selected from the group consisting of nitrogen, oxygen and sulfur as ring member(s) and which may be bonded via a linear or branched C$_{1-6}$ alkylene group; or a 5- to 14-membered aryl or heteroaryl radical, which may be substituted with 1, 2 or 3 substituent(s) independently selected from the group consisting of —CF$_3$, —C$_{1-5}$-alkyl, —O—C$_{1-5}$-alkyl, —S—C$_{1-5}$-alkyl, —C(=O)—OH, —C(=O)—O—C$_{1-5}$-alkyl, —O—C(=O)—C$_{1-5}$-alkyl, F, Cl, Br, I, —CN, —OCF$_3$, —SCF$_3$, —OH, —SH, —NH$_2$, —NH(C$_{1-5}$-alkyl), —N(C$_{1-5}$-alkyl)$_2$, —NH—C(=O)—C$_{1-5}$-alkyl, —N(C$_{1-5}$-alkyl)-C(=O)—C$_{1-5}$-alkyl, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched C$_{1-6}$ alkylene, C$_{2-6}$ alkenylene or C$_{2-6}$ alkinylene group and wherein the heteroaryl radical contains 1, 2 or 3 heteroatom(s) independently selected from the group consisting of nitrogen, oxygen and sulfur as ring member(s);

with the condition that when R$^9$ and R$^{9a}$ form a saturated, unsaturated or aromatic 3 to 9-membered heterocyclic ring optionally substituted, R$^6$ does not represent —S(=O)$_2$—N(R$^{14}$)R$^{15}$.

or a pharmaceutically acceptable salt, isomer, prodrug or solvate thereof
optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof, or a corresponding solvate thereof.

In a preferred embodiment when R$^9$ and R$^{9a}$ form a saturated, unsaturated or aromatic 3 to 9-membered heterocyclic ring optionally substituted, none of R$^5$, R$^6$, R$^7$ or R$^8$ represent —S(=O)$_2$—N(R$^{14}$)R$^{15}$.

The term "salt" must be understood as any form of an active compound used in accordance with this invention in which the said compound is in ionic form or is charged and coupled to a counter-ion (a cation or anion) or is in solution. This definition also includes quaternary ammonium salts and complexes of the active molecule with other molecules and ions, particularly complexes formed via ionic interactions. The definition particularly includes physiologically acceptable salts; this term must be understood as equivalent to "pharmacologically acceptable salts".

The term "physiologically acceptable salts" in the context of this invention means any salt that is tolerated physiologically (normally meaning that it is not toxic, particularly as a result of the counter-ion) when used in an appropriate manner for a treatment, particularly applied or used in humans and/or mammals.

These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations (NH$_4^+$). Preferred salts are those formed with (mono) or (di)sodium, (mono) or (di)potassium, magnesium or calcium.

These physiologically acceptable salts may be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methansulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bound by a non-covalent bond to another molecule (normally a polar solvent), especially including hydrates and alcoholates, for example methanolate.

In another preferred embodiment of the invention A represents:

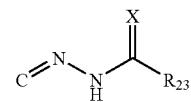

which means (Ib) type compounds:

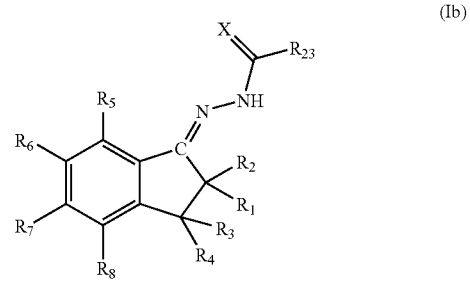

being X an NH and R$^{23}$ an NH2.

In another preferred embodiment of the invention A represents:

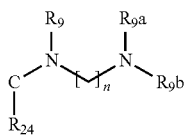

which means (Ia) type compounds:

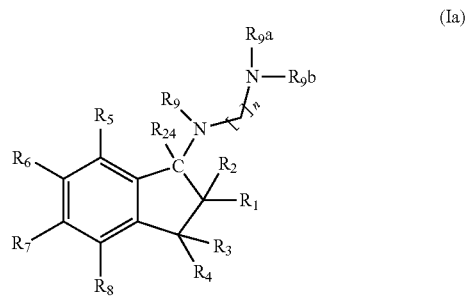

wherein $R_{24}$ represents an hydrogen atom, $R_{9b}$ represents a hydrogen atom or a saturated $C_{1-5}$ aliphatic radical and $R_9$ together with $R_{9a}$ represent a saturated or aromatic 3 to 9 membered heterocyclic ring.

Another preferred embodiment of the invention defines those compounds of formula I wherein at least one of $R^5$, $R^6$, $R^7$ and $R^8$ represents a —N($R_{16}$)—S(=O)$_2$—$R_{17}$ radical having $R^{16}$ and $R^{17}$ the meaning above mentioned.

Another preferred embodiment are compounds of formula I wherein at least one of $R^5$, $R^6$, $R^7$ and $R^8$ represents a —S(=O)$_2$—N($R^{14}$)$R^{15}$ radical wherein at least one of $R^{14}$ and $R^{15}$ represents a 5- to 14-membered aryl or heteroaryl radical which may be substituted and wherein the heteroaryl radical contains 1, 2 or 3 heteroatom(s) independently selected from the group consisting of nitrogen, oxygen and sulphur as ring member(s). In this embodiment the 5- to 14-membered aryl or heteroaryl radical is preferably substituted by Cl.

Another preferred embodiment are compounds of formula I wherein $R_1$, $R_2$, $R_3$ and $R_4$ represent an hydrogen atom or and $C_{1-5}$ aliphatic radical, $R_5$, $R_6$, $R_7$ and $R_8$ represent an —S(=O)$_2$—N($R^{14}$)$R^{15}$ radical or an —N($R_{16}$)—S(=O)$_2$—$R_{17}$ radical, being $R_{14}$, $R_{15}$, $R_{16}$ and $R_{17}$ a 5- to 14-membered aryl or heteroaryl radical optionally substituted with Cl and wherein the heteroaryl radical contains 1, 2 or 3 heteroatom(s) independently selected from the group consisting of nitrogen, oxygen and sulphur as ring member(s), and A represents

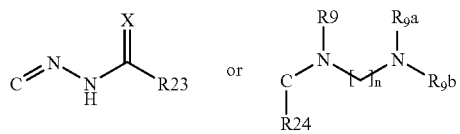

where X represents NH and $R_{23}$ represents NH2 and where $R_{24}$ represents an hydrogen atom, $R_{9b}$ represents a hydrogen atom or a linear saturated $C_{1-5}$ aliphatic radical and $R_9$ together with $R_{9a}$ represent a saturated or aromatic 3 to 9 membered heterocyclic ring.

Among all the compounds described in the general formula I, particularly preferred are any of those selected from:

[1] N-[2-methyl-3-(4-methylpiperazin-1-yl)-2,3-dihydro-1H-inden-5-yl]naphtalene-2-sulfonamide
[2] N-[3-(4-methylpiperazin-1-yl)-2,3-dihydro-1H-inden-5-yl]naphtalene-2-sulfonamide
[3] N-[3-(4-methylpiperazin-1-yl)-2,3-dihydro-1H-inden-5-yl]-5-chloro-3-methylbenzo[b]thiophene-2-sulfonamide
[4] N-[3-(4-methylpiperazin-1-yl)-2,3-dihydro-1H-inden-5-yl]-6-chloroimidazo[2,1-b][1,3]thiazole-5-sulfonamide
[5] N-[3-(piperazin-1-yl)-2,3-dihydro-1H-inden-5-yl]-6-chloroimidazo[2,1-b][1,3]thiazole-5-sulfonamide
[6] N-[1-(4-methylpiperazin-1-yl)-2,3-dihydro-1H-inden-4-yl]-6-chloroimidazo[2,1-b][1,3]thiazole-5-sulfonamide
[7] N-[5-methoxy-1-(4-methylpiperazin-1-yl)-2,3-dihydro-1H-inden-4-yl]-5-chloro-3-methylbenzo[b]thiophene-2-sulfonamide
[8] 2-{6-[(2-naphthylsulfonyl)amino]-2,3-dihydro-1H-inden-1-ylidene}hydrazinecarboximidamide hydrochloride
[9] 2-(6-{[(6-chloroimidazo[2,1-b][1,3]thiazol-5-yl)sulfonyl]amino}-2,3-dihydro-1H-inden-1-ylidene)hydrazinecarboximidamide
[10] 2-(4-{[(6-chloroimidazo[2,1-b][1,3]thiazol-5-yl)sulfonyl]amino}-2,3-dihydro-1H-inden-1-ylidene)hydrazinecarboximidamide
[11] 2-(6-{[(6-chloroimidazo[2,1-b][1,3]thiazol-5-yl)sulfonyl]amino}-2-methyl-2,3-dihydro-1H-inden-1-ylidene)hydrazinecarboximidamide
[12] (+)-N-[3-(4-methylpiperazin-1-yl)-2,3-dihydro-1H-inden-5-yl]-6-chloroimidazo[2,1-b][1,3]thiazole-5-sulfonamide
[13] (−)-N-[3-(4-methylpiperazin-1-yl)-2,3-dihydro-1H-inden-5-yl]-6-chloroimidazo[2,1-b][1,3]thiazole-5-sulfonamide A specific embodiment of the invention is that in which the indanyl sulphonamide compounds of the invention represent a compound with the general formula (Ia):

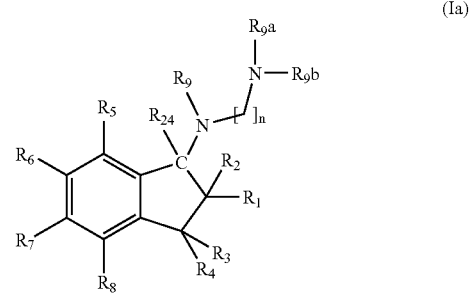

where $R^1$, $R^2$, $R^3$, $R^4$, $R^5$, $R^6$, $R^7$, $R^8$, $R^9$, $R^{9a}$, $R^{9b}$, $R^{24}$ have the previously mentioned meanings and n=1, 2, 3 or 4.

Also a specific embodiment is one in which the indanyl sulphonamide compounds of the invention are represented by the general formula (Ib):

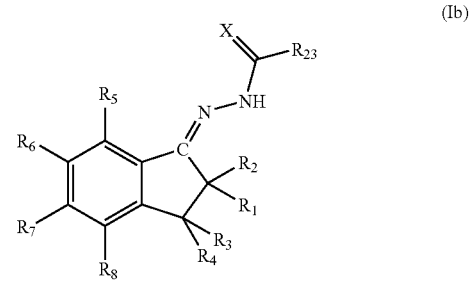

where $R^1$, $R^2$, $R^3$, $R^4$, $R^5$, $R^6$, $R^7$, $R^8$, $R^{23}$ and X have the previously mentioned meanings.

In a different aspect, the invention refers to processes for preparing the indanyl sulfonamides compounds of general formula I. Two processes have been developed for obtaining the indanyl sulfonamides compounds of the invention. Each of these procedures will be explained below.

Method A

First of all, a process is described for producing indanyl sulfonamide compounds of general formula (Ia):

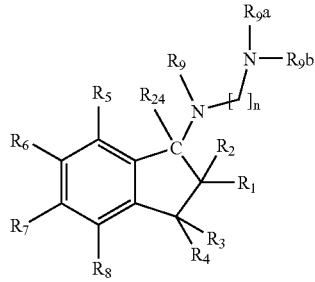
(Ia)

where $R^1, R^2, R^3, R^4, R^5, R^6, R^7, R^8, R^9, R^{9a}, R^{9b}, R^{24}$ have the previously mentioned meanings and n=1, 2, 3 or 4 that comprises the following steps:

a) reacting an indanone of general formula (II):

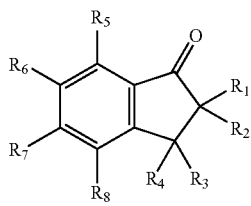
(II)

where $R_1, R_2, R_3, R_4, R_5, R_6, R_7$ and $R_8$ have the meaning given above, with a compound of formula (III):

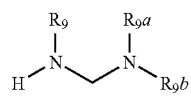
(III)

where $R^9, R^{9a}$ and $R^{9b}$ have the meaning given above in the presence of a Lewis acid at a temperature between 50° C. and 70° C., b) reduction of the material resulting from step a) with a reducing agent in a suitable solvent at reflux.

In the first step, suitably substituted 1-indanone of general formula (II) is reacted with a suitably substituted compound of general formula (III). The reaction is carried out in the presence of a Lewis acid, preferably titanium (IV) isopropoxide at temperatures between 50 and 70° C. for a suitable period of time. The resulting material is reduced with a solution of sodium borohydride in ethanol at reflux for a suitable period of time. The isolation of the compound of general formula (Ia) can be achieved by adding a solution of sodium carbonate in water, filtration and concentrating the filtrate at reduced pressure. The product recovered is then purified by chromatography if necessary.

Method B

Method B represents a process for producing indanyl sulfonamide compounds of general formula (Ib):

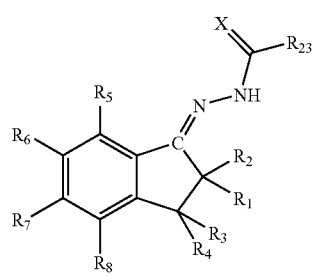
(Ib)

where $R^1, R^2, R^3, R^4, R^5, R^6, R^7, R^8, R^{23}$ and X have the previously mentioned meanings, that comprises reacting an indanone of general formula (II):

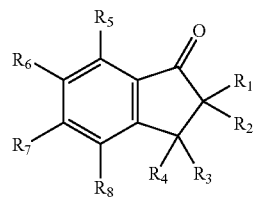
(II)

where $R_1, R_2, R_3, R_4, R_5, R_6, R_7$ and $R_8$ have the meaning given above, with a compound of formula (IV):

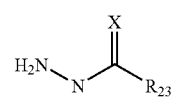
(IV)

where $R_{23}$ and X have the meaning given above, in the presence of a suitable solvent in an acid medium at reflux.

The compounds with the general formula (Ib) can be prepared by reacting a suitably substituted 1-indanone of general formula (II) with a compound of general formula (IV). The reaction is carried out in the presence of an organic solvent, particularly methanol or acetonitrile. The reaction takes place in an acid medium, preferably hydrochloric acid at reflux temperature for a suitable period of time. The resulting compound of general formula (Ib) can be isolated by evaporating the solvent and purified, if necessary, by recrystallisation from a suitable solvent.

Methods A and B are represented in the following scheme:

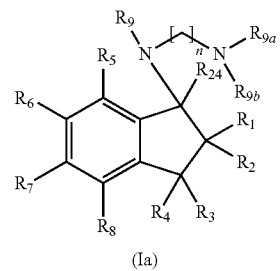
(Ia)

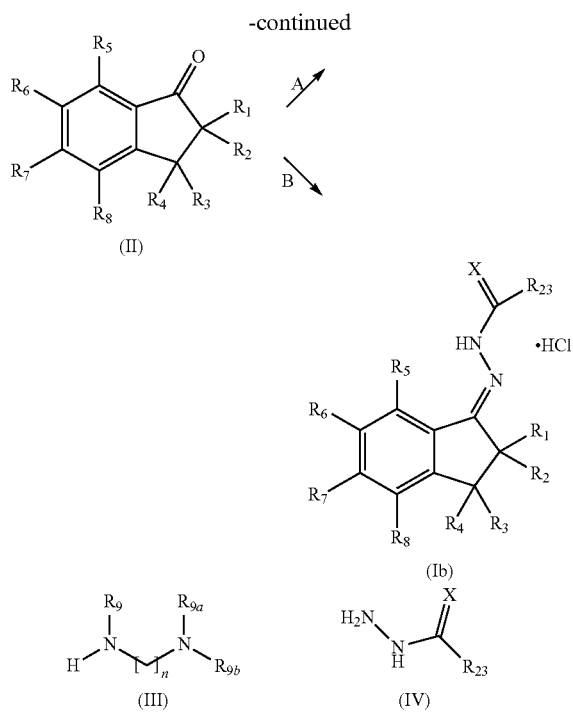

Another essential aspect of the invention is the intermediates compounds of general formula (II):

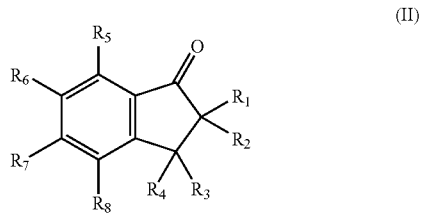

where $R^1$, $R^2$, $R^3$, $R^4$, independent from one another, each represent an hydrogen atom; or a linear or branched, saturated or unsaturated $C_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$;

$R^5$, $R^6$, $R^7$ and $R^8$, independent from one another, each represent a hydrogen atom; —NO$_2$; —NH$_2$; —SH; —OH; —CN; —C(=O)—H; —C(=O)—R$^{10}$; —OR$^{11}$; —SR$^{12}$; —S(=O)$_2$—N(R$^{14}$)R$^{15}$; —N(R$^{16}$)—S(=O)$_2$—R$^{17}$; —NH—R$^{18}$; —NR$^{19}$R$^{20}$; F; Cl, Br; I; a linear or branched, saturated or unsaturated $C_{1-6}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$; or a 5- to 14-membered aryl or heteroaryl radical, which may be substituted with 1, 2 or 3 substituent(s) independently selected from the group consisting of —CF$_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —OCF$_3$, —SCF$_3$, —OH, —SH, —NH$_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —NO$_2$, —CHO, —CF$_2$H, —CFH$_2$, —C(=O)—NH$_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched $C_{1-6}$ alkylene group and wherein the heteroaryl radical contains 1, 2 or 3 heteroatom(s) independently selected from the group consisting of nitrogen, oxygen and sulfur as ring member(s).

These compounds are useful for obtaining the compounds of general formula (I) and can be prepared according to the process described in U.S. 60/735,042.

An additional aspect of the invention relates to the therapeutic use of the compounds of general formula (I). As already mentioned, indanyl sulphonamide compounds of general formula (I) have a strong affinity to 5-HT$_6$ receptors and can behave as agonists, antagonists, inverse agonists, partial antagonists or partial agonists thereof. For this reason, they are suitable for the treatment and the prophylaxis of disorders and diseases mediated by 5HT$_6$ receptors. In this sense, indene derivatives of general formula I are particularly useful for disorders or diseases related to food intake, preferably for appetite regulation, maintaining, increasing or reducing body weight, for prophylaxis and/or treatment of obesity, bulimia, anorexia, cachexia or diabetes type II, or for the prophylaxis and/or treatment of irritable bowel syndrome; disorders of the central nervous system; anxiety; panic attacks; depression; bipolar disorders; cognitive disorders; memory disorders; senile dementia; psychosis; schizophrenia; neurodegenerative disorders preferably selected among Alzheimer's disease, Parkinson's disease, Huntington's disease and multiple sclerosis; or hyperactivity disorders, preferably attention deficit/hyperactivity disorder, or for improving cognitive capacity.

Another essential aspect of the invention is a pharmaceutical composition that comprises a compound of general formula (I) and at least one additive and/or auxiliary material that is pharmaceutically acceptable.

The auxiliary material and/or additive can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, oral, sublingual, nasal, percutaneous, vaginal, oral or parenteral application.

Suitable preparations for oral applications are pills, chewing gums, capsules, granules, drops or syrups.

Suitable preparations for parenteral applications are solutions, suspensions, reconstitutable dry preparations or sprays.

The compounds of the invention as deposits in dissolved form or in patches, optionally with agents that promote skin penetration, are examples of means of percutaneous application.

Skin applications include ointments, gels, creams, lotions, suspensions or emulsions.

The preferred form of rectal application is by means of suppositories.

Optionally, the compositions in accordance with the invention can have a slow release rate in the aforementioned applications, particularly for oral, rectal and percutaneous applications.

The amount of active ingredient that must be administered to the patient depends on the patient's weight, the type of application, the condition and severity of the disease. Normally, in human beings 1 to 500 mg of the active compound are administered daily in one or several doses.

Described below are a number of examples by way of illustration of the invention:

EXAMPLE 1

Synthesis of N-[3-(4-methylpiperazin-1-yl)-2,3-dihydro-1H-inden-5-yl]-5-chloro-3-methylbenzo[b]thiophene-2-sulfonamide (compound 3) by method A A mixture of N-(3-oxo-2,3-dihydro-1H-inden-5-yl)-5-chloro-3-methylbenzo[b]thiophene-2-sulfonamide (100 mg, 0.26 mmol), 1-methylpiperazine (0.28 ml, 2.6 mmol) and titanium (IV) isopropoxide (0.1 ml, 0.33 mmol) was heated at 50° C. for 30 min. The material was dissolved in ethanol and sodium borohydride (11 mg, 0.29 mmol) was added. After stirring at reflux for 3 hours, 2N sodium carbonate was added. The mixture was filtered and the filtrate was concentrated in vacuo. The resulting crude was purified by chromatography on silica gel, using as an eluent mixtures of methylene chloride/methanol/ammonia yielding 80 mg (65%) of N-[3-(4-methylpiperazin-1-yl)-2,3-dihydro-1H-inden-5-yl]-5-chloro-3-methylbenzo[b]thiophene-2-sulfonamide as a solid.

EXAMPLE 2

Synthesis of 2-{6-[(2-naphthylsulfonyl)amino]-2,3-dihydro-1H-inden-1-ylidene}hydrazinecarboximidamide hydrochloride (compound 8) by method B Aminoguanidine hydrogencarbonate (45 mg, 0.33 mmol) was dissolved in 2 ml of 1 N HCl. A solution of N-(3-oxo-2,3-dihydro-1H-inden-5-yl)naphthalene-2-sulfonamide (100 mg, 0.30 mmol) in methanol (2 ml) was added and the mixture was heated to reflux for 1 hour. Then the mixture was concentrated in vacuo and the precipitated salt was crystallized from acetonitrile to give 48 mg (36%) of 2-{6-[(2-naphthylsulfonyl)amino]-2,3-dihydro-1H-inden-1-ylidene}hydrazinecarboximidamide hydrochloride.

EXAMPLE 3

Preparation of (+)-N-[3-(4-methylpiperazin-1-yl)-2,3-dihydro-1H-inden-5-yl]-6-chloroimidazo[2,1-b][1,3]thiazole-5-sulfonamide (compound 12) and (−)-N-[3-(4-methylpiperazin-1-yl)-2,3-dihydro-1H-inden-5-yl]-6-chloroimidazo[2,1-b][1,3]thiazole-5-sulfonamide (compound 13) by HPLC resolution The enantiomers 12 (+) and 13 (−) were separated from racemic N-[3-(4-methylpiperazin-1-yl)-2,3-dihydro-1H-inden-5-yl]-6-chloroimidazo[2,1-b][1,3]thiazole-5-sulfonamide (compound 4) by semipreparative HPLC (Chiralpak AD-H, 5µ, 2×25 cm column; heptane/ethanol 0.1% Et$_2$NH, 85/15 v/v mobile phase; flow-rate 13 ml/min; λ=220 nm; 0.5 ml injection volume, solution 20 mg/ml). The eluates were evaporated. Compound 12: Rt=25 min, $[\alpha]_D^{25° C.}$=+55.2. Compound 13: Rt=20 min, $[\alpha]_D^{25° C.}$=−57.8.

Melting point and the spectroscopic data obtained from some of the compounds of general formula I prepared in accordance with the examples are shown in the following table:

| Cpd | COMPOUND | M. p. (° C.) | IR (cm$^{-1}$) | $^1$H-NMR, δ (solvent) | $[\alpha]_D^{25° C.}$ |
|---|---|---|---|---|---|
| 1 | | Oil | NaCl: 3056, 2931, 1331, 1160 | 300 MHz (CDCl$_3$): 1.06-1.13 (m, 3H), 2.20-2.51 (m, 13H), 2.92-2.97 (m, 1H), 3.64-3.85 (m, 1H), 6.91 (s, 1H), 7.54-7.63 (m, 2H), 7.71-7.76 (m, 1H), 7.84-7.91 (m, 3H), 8.30-8.35 (m, 1H) | — |
| 2 | | 179-80 | KBr: 3432, 2938, 2842, 1327, 1159 | 300 MH, (CDCl$_3$): 1.92-1.99 (m, 2H), 2.19-2.25 (m, 8H), 2.29-2.35 (m, 2H), 2.59-2.82 (m, 3H), 4.15 (t, J=7 Hz, 1H), 6.99-7.05 (m, 3H), 7.51-7.62 (m, 2H), 7.76-7.89 (m, 4H), 8.31 (s, 1H) | — |

-continued

| Cpd | COMPOUND | M.p. (° C.) | IR (cm⁻¹) | ¹H-NMR, δ (solvent) | $[\alpha]_D^{25°\,C.}$ |
|---|---|---|---|---|---|
| 3 | (5-chloro-3-methylbenzothiophene-2-sulfonamide linked to indanyl-4-methylpiperazine) | 217-8 | KBr: 3435, 2934, 2842, 1322, 1156 | 300 MHz, (CDCl₃): 1.99-2.07 (m, 2H), 2.29-2.32 (m, 6H), 2.38 (s, 3H), 2.45-2.48 (m, 2H), 2.67-2.89 (m, 2H), 4.23 (t, J=7 Hz, 1H), 6.99 (s, 1H), 7.03-7.12 (m, 2H), 7.41-7.44 (m, 1H), 7.69-7.72 (m, 2H) | — |
| 4 | (6-chloroimidazo[2,1-b]thiazole-5-sulfonamide linked to indanyl-4-methylpiperazine) | 110-1 | KBr: 3429, 2942, 2845, 1460, 1244 | 300 MHz (CDCl₃): 1.97-2.05 (m, 2H), 2.28-2.48 (m, 11H), 2.69-2.81 (m, 2H), 4.21 (t, J=7 Hz, 1H), 6.92 (d, J=4 Hz, 1H), 7.04-7.05 (m, 3H), 7.73 (d, J=4 Hz, 1H) | — |
| 5 | (6-chloroimidazo[2,1-b]thiazole-5-sulfonamide linked to indanyl-piperazine) | 216-7 | KBr: 3389, 3114, 2958, 2846, 1485, 1270 | 400 MHz (DMSO-d₆): 1.84-1.92 (m, 2H), 2.07-2.29 (m, 2H), 2.41-2.44 (m, 2H), 2.50-2.60 (m, 1H), 2.64-2.70 (m, 1H), 2.78-2.87 (m, 4H), 4.08 (t, J=7 Hz, 1H), 6.75-6.80 (m, 2H), 6.91 (d, J=8 Hz, 1H), 7.43 (d, J=4 Hz, 1H), 7.88 (d, J=4 Hz, 1H) | — |
| 6 | (6-chloroimidazo[2,1-b]thiazole-5-sulfonamide linked to indanyl-4-methylpiperazine) | 182-3 | KBr: 3433, 2953, 2843, 1460, 1281 | 400 MHz (DMSO-d₆): 1.75-1.80 (m, 2H), 2.12-2.38 (m, 10H), 2.93-2.95 (m, 3H), 4.11 (t, J=7 Hz, 1H), 6.75-6.77 (m, 1H), 6.92 (d, J=4 Hz, 2H), 7.39 (d, J=4 Hz, 1H), 7.69 (d, J=4 Hz, 1H) | — |

| Cpd | COMPOUND | M. p. (° C.) | IR (cm$^{-1}$) | $^1$H-NMR, δ (solvent) | $[α]_D^{25° C.}$ |
|---|---|---|---|---|---|
| 7 | | 221-2 | KBr: 2930, 2834, 1335, 1156, 1069 | 300 MHz (CDCl$_3$): 2.11-2.13 (m, 4H), 2.29 (s, 3H), 2.42-2.62 (m, 8H), 3.05 (s, 3H), 4.30 (t, J=7 Hz, 1H), 6.45 (d, J=8 Hz, 1H), 7.19 (d, J=8 Hz, 1H), 7.43 (dd, J=8 Hz, J=2 Hz, 1H), 7.66 (d, J=2 Hz, 1H), 7.73 (d, J=8 Hz, 1H) | — |
| 8 | | 256-7 | KBr: 3148, 3050, 1675, 1605, 1333, 1153 | 300 MH, (DMSO-d$_6$): 2.94-2.96 (m, 2H), 3.10-3.13 (m, 2H), 7.22 (d, J=8 Hz, 1H), 7.37 (d, J=8 Hz, 1H), 7.78-7.96 (m, 7H), 7.94 (d, J=8 Hz, 1H) 8.16 (d, J= 8 Hz, 1H), 8.23-8.29 (m, 2H), 8.67 (s, 1H), 10.63 (br s, 2H), 11.03 (br s, 2H) | — |
| 9 | | 219-20 | KBr: 3432, 3313, 3116, 1673, 1635, 1246, 1148 | 300 MH, (DMSO-d$_6$): 2.79-2.83 (m, 2H), 2.98-3.01 (m, 2H), 7.04 (d, J=8 Hz, 1H), 7.27 (d, J=8 Hz, 1H), 7.58-7.59 (m, 2H), 7.69 (br s, 3H), 8.05 (d, J=4 Hz, 1H), 11.00 (br s, 2H). | — |
| 10 | | >300 (dec) | KBr: 3469, 3254, 3149, 1676, 1635, 1398, 1139 | 400 MH, (DMSO-d$_6$): 2.58-2.61 (m, 2H), 2.71-2.73 (m, 2H), 6.95 (d, J=8 Hz, 1H), 7.09-7.14 (m, 1H), 7.47 (d, J=4 Hz, 1H), 7.56 (d, J=8 Hz, 1H), 7.68 (br s, 3H), 7.78 (d, J=4 Hz, 1H), 10.56 (br s, 1H), 11.18 (br s, 1H) | — |

-continued

| Cpd | COMPOUND | M. p. (° C.) | IR (cm$^{-1}$) | $^1$H-NMR, δ (solvent) | $[α]_D^{25° C.}$ |
|---|---|---|---|---|---|
| 11 | 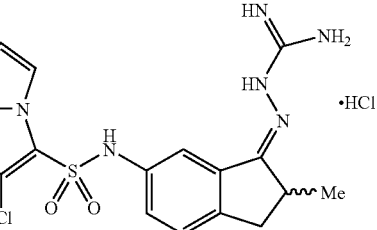 ·HCl | >300 (dec) | KBr: 3425, 3150, 2973, 2801, 1678, 1595, 1250, 1151 | 300 MH, (DMSO-d$_6$): 1.08 (d, J=7 Hz, 3H), 3.20-3.26 (m, 1H), 3.38-3.48 (m, 2H), 7.02 (d, J=8 Hz, 1H), 7.24 (d, J=8 Hz, 1H), 7.57-7.59 (m, 2H), 7.77 (br s, 3H), 8.02 (d, J=4 Hz, 1H), 10.96 (br s, 1H), 11.31 (br s, 1H). | — |
| 12 | 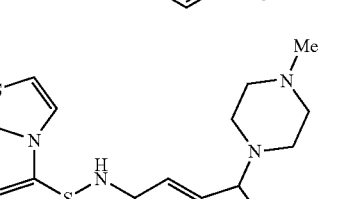 | | | | +55.2 (c 0.5, MeOH) |
| 13 | 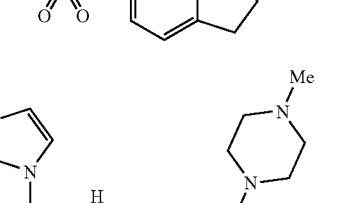 | | | | −57.8 (c 0.5, MeOH) |

Binding Test to 5-HT$_6$ Receptors

Membranes of HEK-293 cells expressing the 5HT$_6$ human recombinant receptor were supplied by Receptor Biology. In these membranes the receptor concentration is 2.18 pmol/mg protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipsychotic Agents to 5-Hydroxytryptamine-6 and Hydroxytryptamine-7 Receptors. *The Journal of Pharmacology and Experimental Therapeutics*, 1994, 268, 1403] with slight modifications. The commercial membrane is diluted (dilution 1:40) with the binding buffer: 50 mM Tris-HCl, 10 mM MgCl$_2$, 0.5 mM EDTA (pH 7.4). The radioligand used is [$^3$H]-LSD at a concentration of 2.7 nM with a final volume of 200 μl. Incubation is initiated by adding 100 μl of the membrane suspension (≈22.9 μg membrane protein), and continues for 60 minutes at a temperature of 37° C. Incubation ends by fast filtration in a Harvester Brandel Cell through glass fibre filters manufactured by Schleicher & Schuell GF 3362 pre-treated with a 0.5% polyethylenimine solution. The filters are washed three times with three milliliters of Tris-HCl 50 mM pH 7.4 buffer. The filters are transferred to phials and to each phial 5 ml of liquid scintillation cocktail Ecoscint H is added. The phials are allowed to reach equilibrium for several hours before being counted in a Wallac Winspectral 1414 scintillation counter. Non-specific binding is determined in the presence of 100 μM serotonin. The tests are performed in triplicate. The inhibition constants (K$_i$, nM) are calculated by non-linear regression analysis using the program EBDA/LIGAND [Munson and Rodbard, *Analytical Biochemistry*, 1980, 107, 220]. The following table shows the binding results for some of the compounds object of the present invention.

| Example | % Inhibition 10$^{-7}$ M | % Inhibition 10$^{-8}$ M |
|---|---|---|
| 2 | 89.1 | 71.6 |
| 3 | 87.9 | 55.7 |
| 4 | 83.4 | 63.0 |
| 5 | 85.6 | 63.6 |
| 8 | 82.2 | 56.1 |
| 9 | 89.6 | 84.7 |
| 11 | 91.1 | 84.7 |

Pharmaceutical Formulation

Daily dosage in human medicine lies between 1 mg and 500 mg of product, which can be administered in one or several administrations. The compositions are prepared in forms compatible with the mode of administration used, such as pills, tablets, capsules, suppositories, solutions or suspensions. These compositions are prepared by known methods and comprise between 1 to 60% by weight of the active principle (compound of general formula I) and 40 to 99% by weight of a suitable pharmaceutical vehicle compatible with the active principle and the physical form of the composition used. By way of example, the formula is shown for a pill containing a product of the invention.

Example of formula per pill:

| | | |
|---|---|---|
| Example 9 | 5 mg | |
| Lactose | 60 mg | |
| Crystalline cellulose | 25 mg | |
| Povidone K 90 | 5 mg | |
| Pregelatinised starch | 3 mg | |
| Colloidal silica dioxide | 1 mg | |
| Magnesium stereate | 1 mg | |
| Total weight per pill | 100 mg | |

The invention claimed is:

1. A substituted indanyl sulfonamide compound of general formula I,

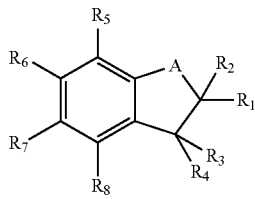

wherein $R^1$, $R^2$, $R^3$, $R^4$, independent from one another, each represent an hydrogen atom; or a linear or branched, saturated or unsaturated $C_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$;

$R^5$, $R^6$, $R^7$ and $R^8$, independent from one another, each represent a hydrogen atom; —NO$_2$; —NH$_2$; —SH; —OH; —CN; —C(=O)—H; —C(=O)—R$^{10}$; —OR$^{11}$; —SR$^{12}$; —S(=O)$_2$—N(R$^{14}$)R$^{15}$, —N(R$^{16}$)—S(=O)$_2$—R$^{17}$; —NH—R$^{18}$; —NR$^{19}$R$^{20}$; F; Cl, Br; I; a linear or branched, saturated or unsaturated $C_{1-6}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$; or a 5- to 14-membered aryl or heteroaryl radical, which may be substituted with 1, 2 or 3 substituent(s) independently selected from the group consisting of —CF$_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —OCF$_3$, —SCF$_3$, —OH, —SH, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —NO$_2$, —CHO, —CF$_2$H, —CFH$_2$, —C(=O)—NH$_2$, —C(=O)—NH ($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched $C_{1-6}$ alkylene group and wherein the heteroaryl radical contains 1, 2 or 3 heteroatom(s) independently selected from the group consisting of nitrogen, oxygen and sulfur as ring member(s);

with the condition that at least one of the substituents $R^5$, $R^6$, $R^7$ and $R^8$ represents a —S(=O)$_2$—N(R$^{14}$)R$^{15}$ or a —N(R$^{16}$)—S(=O)$^2$—R$^{17}$ radical;

A represents

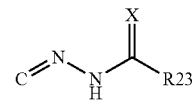

which means (Ib) type compounds:

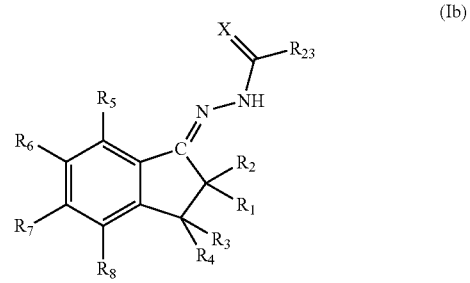

(Ib)

wherein

X represents NH, O or S $R^{23}$ represents NH$_2$ or NH—NH$_2$ $R^{10}$ to $R^{12}$ and $R^{14}$ to $R^{20}$, independent from one another, each represent a hydrogen atom; a linear or branched, saturated or unsaturated $C_{1-5}$ aliphatic radical which may be substituted with 1, 2 or 3 substituent(s) independently selected from the group consisting of F, Cl, Br, —OH, —NH$_2$, —SH, —O—CH$_3$, —O—C$_2$H$_5$, —NO$_2$, —CN, —NH—CH$_3$ and —S—CH$_3$; a saturated or unsaturated 3 to 8-membered cycloaliphatic radical, which may be substituted with 1, 2 or 3 substituent(s) independently selected from the group consisting of $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —CF$_3$, —OCF$_3$, —SCF$_3$, —OH, —SH, —NH$_2$, —NH($C_{1-5}$-alkyl), —N($C_{1-5}$-alkyl)$_2$, —NO$_2$, —CHO, —CF$_2$H, —CFH$_2$, —C(=O)—NH$_2$, —C(=O)—NH ($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may optionally contain 1, 2 or 3 heteroatom(s) independently selected from the group consisting of nitrogen, oxygen and sulfur as ring member(s) and which may be bonded via a linear or branched $C_{1-6}$ alkylene group; or a 5- to 14-membered aryl or heteroaryl radical, which may be substituted with 1, 2 or 3 substituent(s) independently selected from the group consisting of —CF$_3$, $C_{1-5}$-alkyl, —S—$C_{1-5}$-alkyl, —C(=O)—OH, —C(=O)—O—$C_{1-5}$-alkyl, —O—C (=O)—$C_{1-5}$-alkyl, F, Cl, Br, I, —CN, —OCF$_3$, —SCF$_3$, —OH, —SH, —NH$_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, NO$_2$, —CHO, —CF$_2$H, —CFH$_2$, —C(=O)—NH$_2$, —C(=O)—NH ($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched $C_{1-6}$ alkylene, $C_{2-6}$ alkenylene or $C_{2-6}$ alkinylene group and wherein the heteroaryl radical contains 1, 2 or 3 heteroatom(s) independently selected from the group consisting of nitrogen, oxygen and sulfur as ring member(s);
or a pharmaceutically acceptable salt thereof optionally in form of one of its stereoisomers, a racemate or in form of a mixture of at least two of its stereoisomers, in any mixing ratio, or a physiologically acceptable salt thereof.

2. A substituted indanyl sulfonamide compound of general formula I,

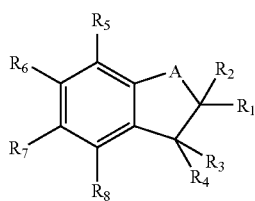
(I)

wherein
$R^1$, $R^2$, $R^3$, $R^4$, K independent from one another, each represent an hydrogen atom; or a linear or branched, saturated or unsaturated $C_{1-5}$ aliphatic radical which may be substituted with 1, 2 or 3 substituent(s) independently selected from the group consisting of F, Cl, Br, —OH, —$NH_2$, —SH, —O—$CH_3$, —O—$C_2H_5$, —$NO_2$, —CN, —NH—$CH_3$ and —S—$CH_3$;
$R^5$, $R^6$, $R^7$ and $R^8$, independent from one another, each represent a hydrogen atom; —$NO_2$; —$NH_2$; —SH; —OH; —CN; —C(=O)—H; —C(=O)—$R^{10}$; —$OR^{11}$; —$SR^{12}$; —S(=O)$_2$—N($R^{14}$)$R^{15}$; —N($R^{16}$)—S(=O)$_2$—$R^{17}$; —NH—$R^{18}$; —$NR^{19}R^{20}$; F; Cl, Br; I; a linear or branched, saturated or unsaturated $C_{1-6}$ aliphatic radical which may be substituted with 1, 2 or 3 substituent(s) independently selected from the group consisting of F, Cl, Br, —OH, —$NH_2$, —SH, —O—$CH_3$, —O—$C_2H_5$, —$NO_2$, —CN, —NH—$CH_3$ and —S—$CH_3$; or a 5- to 14-membered aryl or heteroaryl radical, which may be substituted with 1, 2 or 3 substituent(s) independently selected from the group consisting of —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched $C_{1-6}$ alkylene group and wherein the heteroaryl radical contains 1, 2 or 3 heteroatom(s) independently selected from the group consisting of nitrogen, oxygen and sulfur as ring member(s);
with the condition that at least one of the substituents $R^5$, $R^6$, $R^7$ and $R^8$ represents a —S(=O)$_2$—N($R^{14}$)$R^{15}$ or a —N($R^{16}$)—S(=O)$_2$—$R^{17}$ radical;
A represents

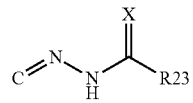

which means (Ib) type compounds:

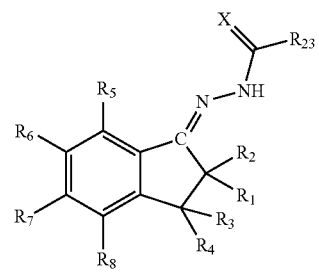
(Ib)

wherein
X represents NH, O or S
$R^{23}$ represents $NH_2$ or NH—$NH_2$
$R^{10}$ to $R^{12}$ and $R^{14}$ to $R^{20}$, independent from one another, each represent a hydrogen atom; a linear or branched, saturated or unsaturated $C_{1-5}$ aliphatic radical which may be substituted with 1, 2 or 3 substituent(s) independently selected from the group consisting of F, Cl, Br, —OH, —$NH_2$, —SH, —O—$CH_3$, —O—$C_2H_5$, —$NO_2$, —CN, —NH—$CH_3$ and —S—$CH_3$; a saturated or unsaturated 3 to 8-membered cycloaliphatic radical, which may be substituted with 1, 2 or 3 substituent(s) independently selected from the group consisting of $C_{1-5}$-alkyl, —O—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may optionally contain 1, 2 or 3 heteroatom(s) independently selected from the group consisting of nitrogen, oxygen and sulfur as ring member(s) and which may be bonded via a linear or branched $C_{1-6}$ alkylene group; or a 5- to 14-membered aryl or heteroaryl radical, which may be substituted with 1, 2 or 3 substituent(s) independently selected from the group consisting of —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy and benzyl and which may be bonded via a linear or branched $C_{1-6}$ alkylene, $C_{2-6}$ alkenylene or $C_{2-6}$ alkinylene group and wherein the heteroaryl radical contains 1, 2 or 3 heteroatom(s) independently selected from the group consisting of nitrogen, oxygen and sulfur as ring member(s);
or a pharmaceutically acceptable salt thereof optionally in form of one of its stereoisomers, a racemate or in form of a mixture of at least two of its stereoisomers, in any mixing ratio, or a physiologically acceptable salt thereof.

3. An indanyl sulfonamide compound according to claim 1 or 2 where X represents NH and $R_{23}$ represents $NH_2$.

4. An indanyl sulfonamide compound according to any of claims 1 or 2 wherein at least one of $R^5$, $R^6$, $R^7$ and $R^8$ represents a —N($R_{16}$)—S(=O)$_2$—$R_{17}$ radical.

5. An indanyl sulfonamide compound according to any of claims 1 or 2 wherein at least one of $R^5$, $R^6$, $R^7$ and $R^8$ represents a —S(=O)$_2$—N($R^{14}$)$R^{15}$ radical.

6. An indanyl sulfonamide compound according to claim 5 wherein at least one of $R^{14}$ and $R^{15}$ represents a 5- to 14-membered aryl or heteroaryl radical which may be substituted and wherein the heteroaryl radical contains 1, 2 or 3 heteroatom(s) independently selected from the group consisting of nitrogen, oxygen and sulphur as ring member(s).

7. An indanyl sulfonamide compound according to claim 6 wherein the 5- to 14-membered aryl or heteroaryl radical is substituted with Cl.

8. An indanyl sulphonamide derivative according to claim 1 wherein $R_1$, $R_2$, $R_3$ and $R_4$ represent an hydrogen atom or and $C_{1-5}$ aliphatic radical, $R_5$, $R_6$, $R_7$ and $R_8$ represent an —S(=O)$_2$—N($R^{14}$)$R^{15}$ radical or an —N($R_{16}$)—S(=O)$_2$—$R_{17}$ radical, being $R_{14}$, $R_{15}$, $R_{16}$ and $R_{17}$ a 5- to 14-membered aryl or heteroaryl radical optionally substituted with Cl and wherein the heteroaryl radical contains 1, 2 or 3 heteroatom(s) independently selected from the group consisting of nitrogen, oxygen and sulphur as ring member(s);

A represents

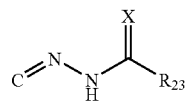

which means (Ib) type compounds:

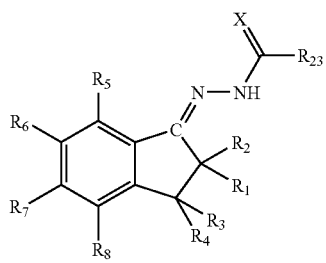

(Ib)

wherein X represents NH and $R_{23}$ represents NH$_2$.

9. An indanyl sulphonamide compound of general formula I according to claim 1, selected from:

[8] 2-{6-[(2-naphthylsulfonyl)amino]-2,3-dihydro-1H-inden-1-ylidene}hydrazinecarboximidamide hydrochloride

[9] 2-(6-{[(6-chloroimidazo[2,1-b][1,3]thiazol-5-yl)sulfonyl]amino}-2,3-dihydro-1H-inden-1-ylidene)hydrazinecarboximidamide

[10] 2-(4-{[(6-chloroimidazo[2,1-b][1,3]thiazol-5-yl)sulfonyl]amino}-2,3-dihydro-1H-inden-1-ylidene)hydrazinecarboximidamide

[11] 2-(6-{[(6-chloroimidazo[2,1-b][1,3]thiazol-5-yl)sulfonyl]amino}-2-methyl-2,3-dihydro-1H-inden-1-ylidene)hydrazinecarboximidamide.

10. Process for producing indanyl sulfonamide compounds of general formula (Ib) according to claim 1 or 2:

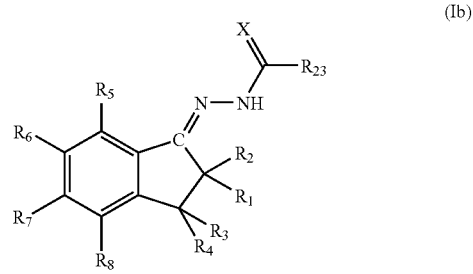

(Ib)

wherein $R^1$, $R^2$, $R^3$, $R^4$, $R^5$, $R^6$, $R^7$, $R^8$, $R^{23}$ and X have the previously mentioned meanings, that comprises reacting an indanone of general formula (II):

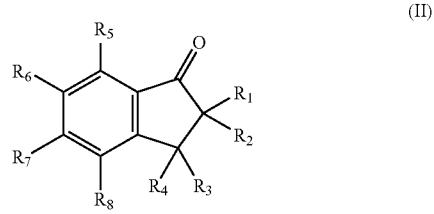

(II)

wherein $R^1$, $R^2$, $R^3$, $R^4$, $R^5$, $R^6$, $R^7$ and $R^8$ have the meaning given above, with a compound of formula (IV):

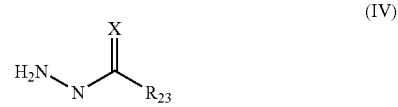

(IV)

wherein $R^{23}$ and X have the meaning given above, in the presence of a suitable solvent in an acid medium at reflux.

11. Process according to claim 10 wherein reaction is carried out with methanol or acetonitrile as solvent and with hydrochloric acid as acid medium.

12. Pharmaceutical composition comprising a compound according to any of claim 1, 2, 8, or 9 and at least a pharmaceutically acceptable additive.

13. An indanyl sulfonamide compound according to any of claim 1 or 2 wherein the stereoisomers are enantiomers and/or diastereomers.

* * * * *